(12) United States Patent
Hare

(10) Patent No.: US 10,798,978 B1
(45) Date of Patent: Oct. 13, 2020

(54) VERSATILE EAR COVER APPARATUS

(71) Applicant: Dorothy Hare, Memphis, TN (US)

(72) Inventor: Dorothy Hare, Memphis, TN (US)

( * ) Notice: Subject to any disclaimer, the term of this patent is extended or adjusted under 35 U.S.C. 154(b) by 530 days.

(21) Appl. No.: 15/338,441

(22) Filed: Oct. 30, 2016

Related U.S. Application Data

(60) Provisional application No. 62/285,025, filed on Oct. 29, 2015.

(51) Int. Cl.
*F41H 1/00* (2006.01)
*A41D 13/05* (2006.01)

(52) U.S. Cl.
CPC .......... *A41D 13/05* (2013.01); *A41D 2400/26* (2013.01)

(58) Field of Classification Search
CPC ........ A41D 13/05; A41D 13/055; A61F 11/06
USPC ............................................................ 2/455
See application file for complete search history.

(56) References Cited

U.S. PATENT DOCUMENTS

| | | | | |
|---|---|---|---|---|
| 2,325,150 | A * | 7/1943 | Sahlmann | A61F 11/06 2/209 |
| 3,249,949 | A * | 5/1966 | Rosenberg | A61F 11/06 2/209 |
| 4,660,229 | A * | 4/1987 | Harris | A61F 11/06 128/866 |
| 6,298,493 | B1 * | 10/2001 | Ambroise | A45D 44/12 128/866 |
| 6,392,196 | B1 * | 5/2002 | Lin | A61F 11/14 2/209 |
| 8,861,771 | B2 * | 10/2014 | Stott | H04R 1/105 181/129 |
| 2003/0085069 | A1 * | 5/2003 | Tsai | A61F 11/06 181/129 |
| 2007/0245459 | A1 * | 10/2007 | Hillman-Schwartz | A45D 44/12 2/209 |
| 2008/0235853 | A1 * | 10/2008 | Sousa | A61F 7/007 2/209 |
| 2010/0303275 | A1 * | 12/2010 | Creek | A61F 11/06 381/380 |
| 2011/0158456 | A1 * | 6/2011 | Voix | A61F 11/12 381/379 |
| 2012/0124719 | A1 * | 5/2012 | Michlitsch | A41D 13/05 2/423 |

* cited by examiner

Primary Examiner — Timothy K Trieu
(74) Attorney, Agent, or Firm — William S. Parks

(57) ABSTRACT

A cover apparatus adapted to cover at least a portion of an ear for protection from the elements, artificial heat sources, and the like, is provided. Such a cover is produced in uniform structure such that any properly sized implement may be affixed to either a left or right ear. Additionally, the manner of affixing is provided through the provision of the ear cover exhibiting sufficient elasticity for pressure fitting around a subject ear auricle and lobe simultaneously, with lower levels of elasticity exhibited by the middle portion thereof extending between the top and bottom portions. Such a cover thus compresses for proper fitting around the auricle and lobe and does not provide excess pressure in the middle portion, thereby allowing for greater comfort and control to the wearer and leaves a least part of the wearer's ear canal exposed and uncovered to facilitate hearing while affixed.

10 Claims, 5 Drawing Sheets

FIG. 1

VERSATILE EAR COVER APPARATUS

CROSS-REFERENCE TO RELATED APPLICATIONS

The present application claims priority to the U.S. Provisional Patent Application No. 62/285,025, filed on Jun. 13, 2016, which was converted from U.S. Non-Provisional patent application Ser. No. 14/927,314, filed on Oct. 29, 2015. The entirety of both the Non-Provisional and Provisional applications are herein incorporated by reference.

FIELD OF THE INVENTION

The disclosure relates to a cover apparatus, and more specifically to a cover apparatus adapted to cover at least a portion of an ear for protection from the elements, artificial heat sources, and the like. Such a cover is produced in uniform structure such that any properly sized implement may be affixed to either a left or right ear. Additionally, the manner of affixing is provided through the provision of the ear cover exhibiting sufficient elasticity for pressure fitting around a subject ear auricle and lobe simultaneously, with lower levels of elasticity exhibited by the middle portion thereof extending between the top and bottom portions. Such a cover thus compresses for proper fitting around the auricle and lobe and does not provide excess pressure in the middle portion, thereby allowing for greater comfort and control to the wearer and leaves a least part of the wearer's ear canal exposed and uncovered to facilitate hearing while affixed. Furthermore, the disclosure may further relate to a method for affixing the apparatus to a subject ear, as well as a means to provide a communication tool (Bluetooth implement, for example) therein.

BACKGROUND OF THE INVENTION

The human ear is highly susceptible to a number of possible problems, particularly as it concerns external temperatures, wind exposure, even excessive sunlight. The sensitive auricle (pinna), including the top outer ear and bottom lobe, extend from the head, leaving little in the way of warmth if in cold locations, and no natural cover, save possibly for a person's hair, if cold. Certain situations have long proven problematic in terms of providing such desirable protections. In particular, as merely as examples, the exposure to the outer ear surfaces to excessive heat under a hair drying bonnet (or even simply when a high temperature hair dryer is utilized in typical fashion), to cold wind and temperatures in snowy regions (particularly if an ear muff is not provided), as well as to ultraviolet rays during sunny days (and the propensity to suffer sunburn on such ear surfaces). With external heat exposure, the subject person is at the mercy of the drying implement itself, with uncomfortable, if not painful, hot air exposure as the result. Ear muffs may protect the entirety of a person's ear in cold temperatures, however, they also reduce the potential for properly hearing certain sounds in such a situation, as well, leaving the subject person in a potential precarious predicament, at least at times. Likewise, the necessity for sun block on certain body parts may not be undertaken for ear surfaces, not to mention the potential for such formulations to wipe or wash off during use; a means to accord an effective cover simply for the exposed ear surfaces could be beneficial without the need to reapply a cream or like composition during an extended time frame. In other words, there has long existed a distinct understanding that ear cover devices are helpful for such purposes. Unfortunately, the typical covers are provided in limited fashion, either, as examples, as metal or hard plastic molded pieces to cover certain parts of the auricle, or as an entirely elastic plastic structure that is limited in structure as to require different manufactured implements for different ears, dependent on the side of the head they are located. Such entirely elastic configurations create, additionally, excessive "grip" over a person's entire outer ear, resulting in implements that either must cover the entire ear canal for proper placement (and thus potentially cause hearing issues while in place) or easily slide off the auricle and lobe upon such placement, leaving the user with having to reapply the implement itself repeatedly during actual use. In any event, there are distinct deficiencies within this art that has left a void for users to rely upon effective applications that allow for proper ear canal exposure (for hearing facilitation while adorned on the wearer, for instance), effective affixation to a wearer (due to properly "gripping" the outer ear with sufficient pressure in specific regions), and the ability to manufacture a single implement that fits either the left or right ear without a user having to determine the correct device at any time. Although the prior art in this area lacks such specific teachings, the present disclosure provides a manner of overcoming these distinct shortcomings.

BRIEF SUMMARY OF THE INVENTION

The disclosure provides an ear cover apparatus. The apparatus may comprise a pouch portion including a top portion, a middle portion, a bottom portion, an opening, and an expandable edge circumnavigating the periphery of the opening. Each of the top portion, the middle portion, and the bottom portion may comprise an interior surface and an exterior surface. The opening may provide a space through which a portion of an ear may be at least partially engulfed by the apparatus, leaving a least a portion of the ear canal uncovered as well. The top portion and bottom portion will exhibit increased levels of elasticity as compared with the middle portions extending therefrom. Elongation of the top and bottom portions of the implement allows for a number of different sized ears to at least partially fit therein as well as localized pressures to be applied on such a subject ear for effective grip and retention thereon. As alluded to above, excessive levels of elasticity, or at least uniform elasticity over the entirety of the implement, will most likely cause problems in terms of the cover itself to contract excessively, rather than to allow for excessive "grip" over the top and bottom portions (outer auricle and bottom lobe, for instance) with less pressure exhibited in the middle portions. In embodiments, then, the implement may provide coverage to at least one portion of an ear adjacent an ear canal (leaving a certain portion of the subject ear canal exposed to facilitate hearing of external sounds by the wearer).

Alternative embodiments may provide an ear cover apparatus including an interior pocket. The interior pocket may be either partially or fully encompassed within the pouch portion of the apparatus and may include an opening, an interior surface and an exterior surface. In embodiments, the interior pocket may expand to provide an internal area that may at least partially house items utilized in conjunction with ears such as, but not limited to Bluetooth devices, headphones, and hearing aids.

The disclosure may provide a method. The method may comprise providing an ear cover. The ear cover may comprise a pouch portion comprising an interior pocket, an opening, and an expandable edge circumnavigating the periphery of the opening. At least a portion of the electronic device may then be inserted into the interior pocket. The ear cover may then be affixed to at least a portion of an ear adjacent an ear canal.

The disclosure may further provide an alternative method. The method may comprise providing an ear cover. The ear cover may comprise a pouch portion comprising an interior pocket, an opening, and an expandable edge circumnavigating the periphery of the opening. The ear cover may then be affixed to at least a portion of an ear adjacent an ear canal. The method may further comprise inserting the interior pocket to the electronic device adjacent the at least a portion of an ear.

The ear covers disclosed herein are also produced, in embodiments, as uniform structures, having the same top and bottom configurations (including elasticity levels therein) and the same extended middle portion configurations (with lower elastic levels). Certainly, different sizes of such covers may be provided (produced) on behalf of different wearers (such as larger covers for adults and smaller for children, as examples), but the overall configurations thereof may be provided, as noted above, in uniform structure (albeit in such different sizes) to accord users and manufacturers the benefit of supplying a single unit (for each size) that covers either side ear on demand. In other words, compared with other ear covers in the past, particularly those that require specific structural components to fit on a specific side ear (whether left or right of a person), the ear covers disclosed herein are simply provided with the pouch, top and bottom portions of higher elasticity levels than the extended middle portions, and the one shape fits either side ear is provided. Likewise, the disclosure herein pertains potentially in embodiments to covers that are not only manufactured in such a manner for either side ear, but they may also be symmetrical in terms of the structural aspects of the top and bottom portions thereof (and thus may exhibit the same shape, curve, elasticity, etc., between both opposing portions of the same cover). Such a situation may further facilitate manufacturer and utilization thereof, if desired, although is not required. Such a pocket portion, then, may be provided within the structure of a disclosed ear cover such that a communication device (Bluetooth, amplifier, ear bud, hearing aid, and the like) may be introduced therein for close proximity and effective retention adjacent to and/or in contact with the user's ear canal. As above, such a pocket may be uniformly configured for either side ear to be utilized in association therewith to the whim of the wearer.

These and other aspects of the disclosed subject matter, as well as additional novel features, will be apparent from the description provided herein. The intent of this summary is not to be a comprehensive description of the subject matter, but rather to provide a short overview of some of the subject matter's functionality. Other systems, methods, features and advantages here provided will become apparent to one with skill in the art upon examination of the accompanying FIGURES and detailed description. It is intended that all such additional systems, methods, features and advantages that are included within this description, be within the scope of any claims filed now and/or later.

BRIEF DESCRIPTION OF THE DRAWINGS

The novel features believed characteristic of the disclosed subject matter will be set forth in any claims that are filed now and/or later. The disclosed subject matter itself, however, as well as a preferred mode of use, further objectives, and advantages thereof, will best be understood by reference to the following detailed description of an illustrative embodiment when read in conjunction with the accompanying drawings, wherein:

DETAILED DESCRIPTION OF THE ILLUSTRATIVE EMBODIMENTS

Reference now should be made to the drawings, in which the same reference numbers are used throughout the different FIGURES to designate the same components.

It will be understood that, although the terms first, second, third, etc. may be used herein to describe various elements, these elements should not be limited by these terms. These terms are only used to distinguish one element from another element. Thus, a first element discussed below could be termed a second element without departing from the teachings of the present disclosure.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The terms "cover", "apparatus", and "implement" are used interchangeably herein to describe the disclosed structure to that effect.

Figure 1:
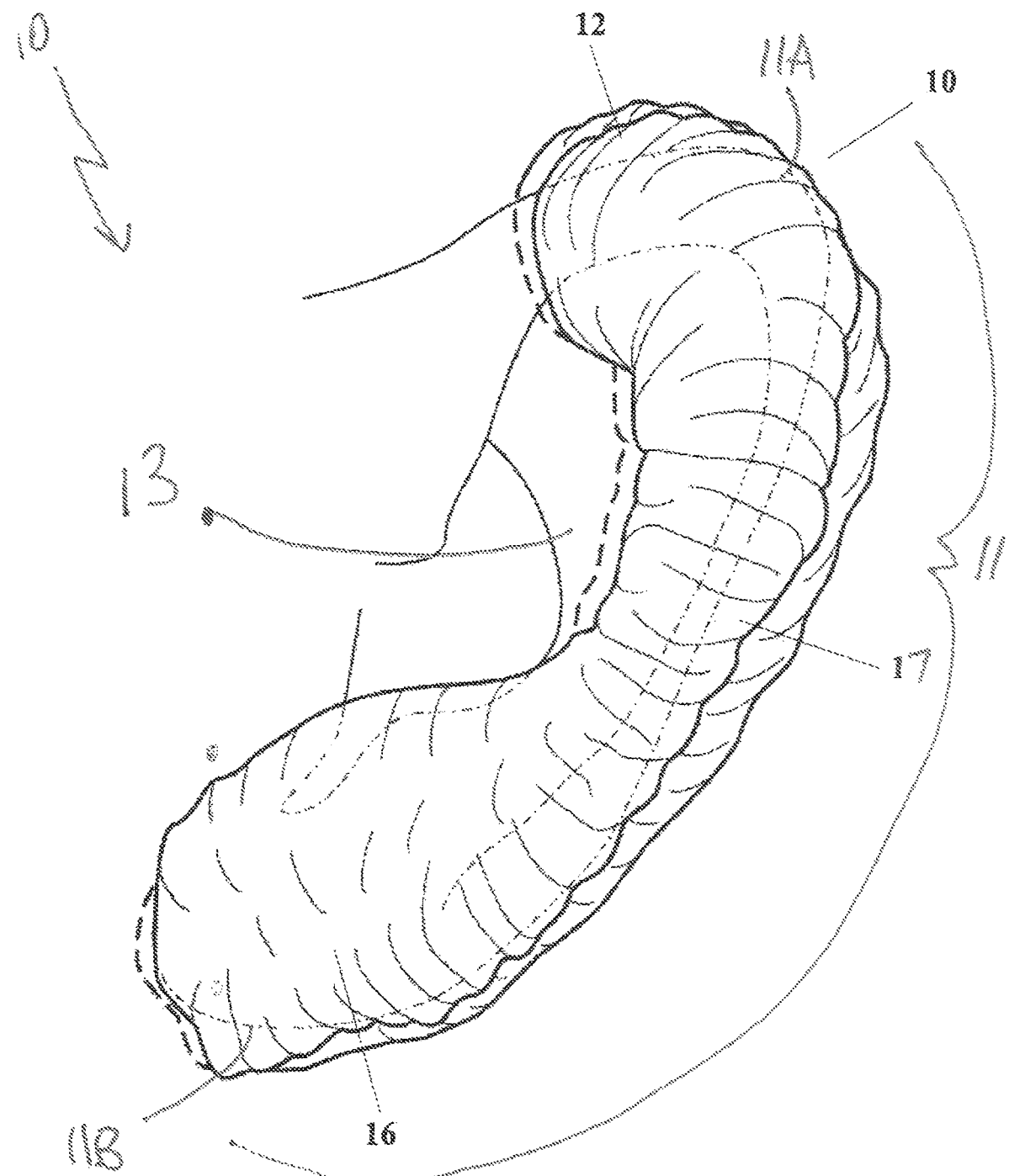
FIG. 1 depicts a perspective view of an ear cover apparatus covering at least a portion of an ear in accordance with embodiments.
Figure 2:
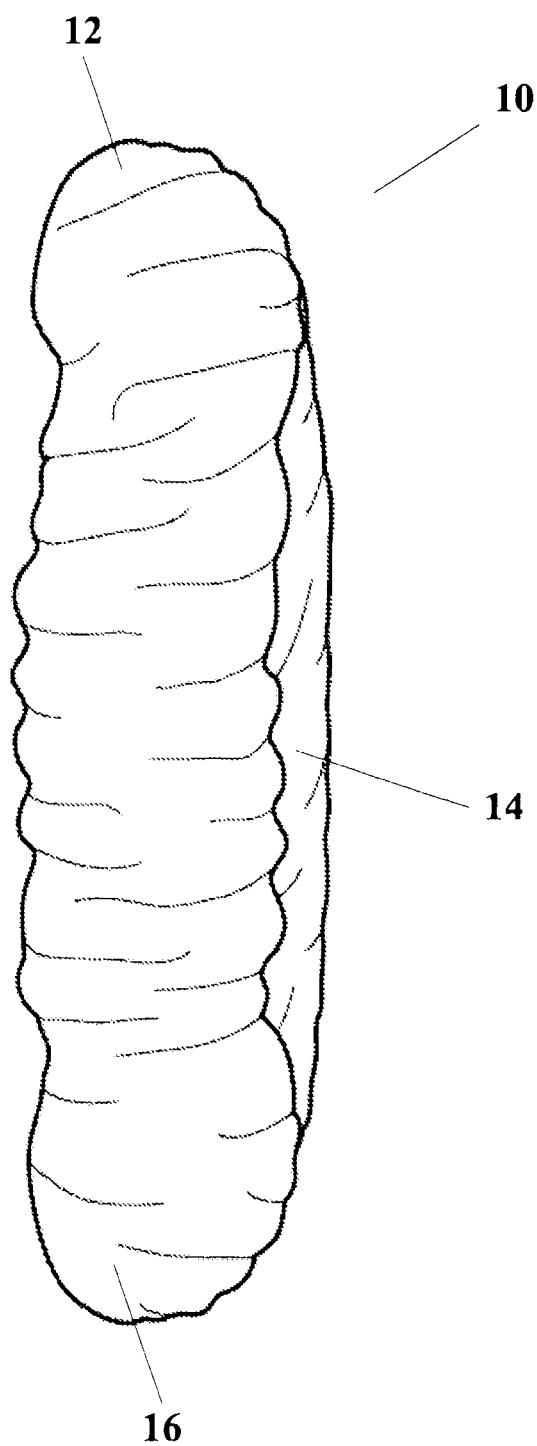
FIG. 2 depicts a side view of an ear cover apparatus in accordance with embodiments.
Figure 3:
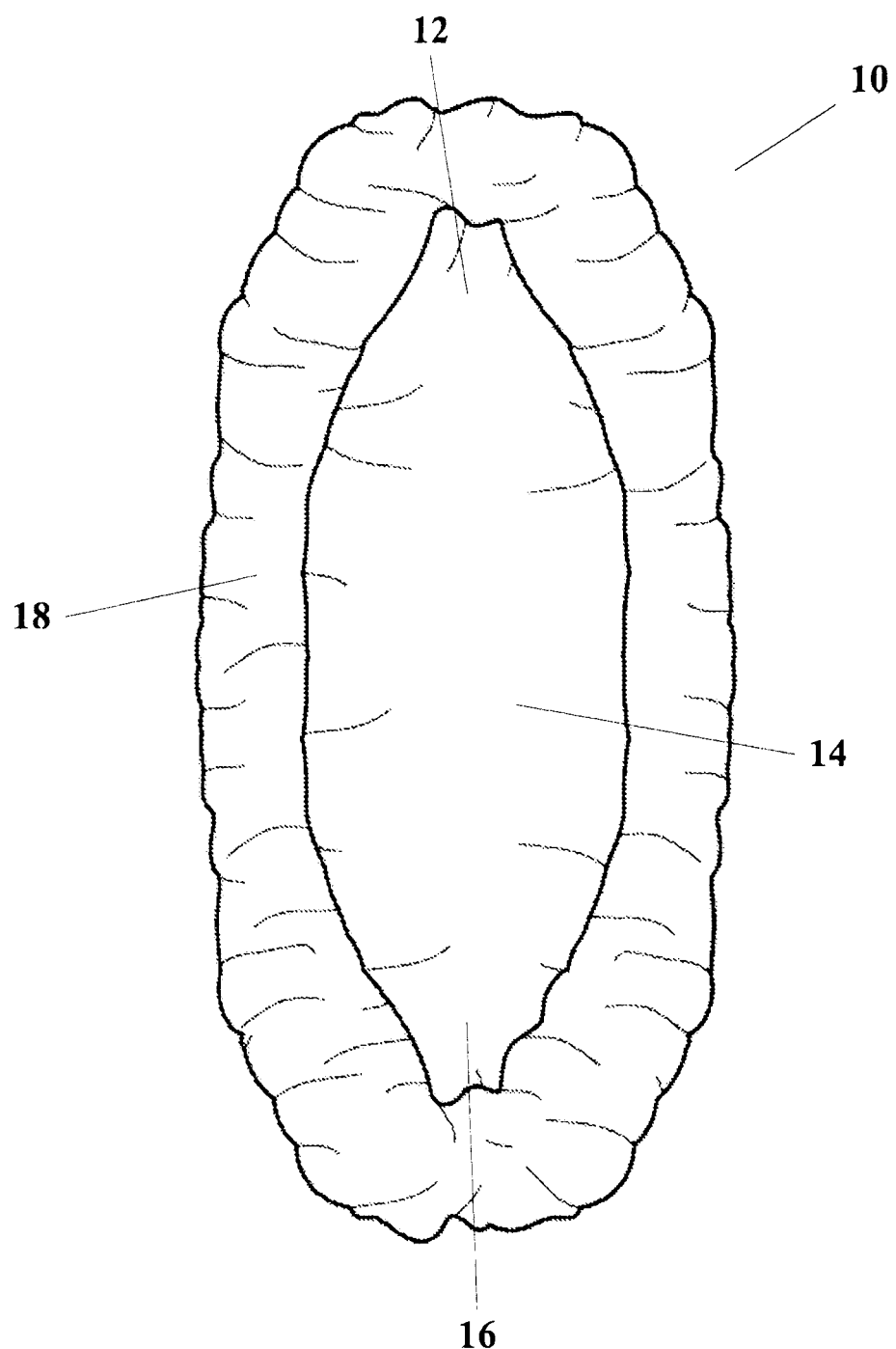
FIG. 3 depicts a front interior view of an ear cover apparatus including an interior pocket in accordance with embodiments.

FIGS. 1-3 depict different perspective views of an ear cover apparatus 10 covering at least a portion of an ear 11, and leaving exposed at least a portion of an ear canal 13, in accordance with embodiments. The apparatus 10 may comprise a pouch portion 14 including a top portion 12, a middle portion 17, a bottom portion 16, an opening (19 of FIG. 3), and an expandable edge circumnavigating the periphery of the opening (15 of FIG. 3). Each of the top portion 12, the middle portion 17, and the bottom portion 16 may comprise an interior surface and an exterior surface. The opening 19 may provide a space through which a portion of an ear 11 may be at least partially engulfed by the apparatus 10, with the top portion 12 covering the upper pinna 11A and the bottom portion 16 covering the lobe 11B, leaving the ear canal 13 at least partially exposed. The top portion 12 and bottom portion 16 may be greater in elasticity than the middle portion 17 (and may, in certain embodiments, be uniform in such a measurement between the top and bottom portions 12, 16). Elongation of the apparatus may allow for a number of different sized ears to at least partially fit within the apparatus without increasing the applied pressure to the overall outer ear (which may, as noted above, contract to too great a degree and cause the implement to dislodge easily from its application). The elastic levels of the top 12 and bottom 16 portions provide sufficient (and high levels of) strength to generate application force to the ear by the implement 10 itself for secure and long-term retention thereon, in other words (and, again, too great an overall application level from the middle portion 17 will cause contraction over the ear, compromising the overall retention effect). In embodiments, the apparatus 10 may provide coverage to at least one portion of an ear adjacent an ear canal 13, thus leaving a least a portion thereof exposed and uncovered (that may provide the wearer with a better way of hearing any external sounds while wearing the implement or implements). In embodiments, the top portion and bottom portion may be greater in elasticity than the middle portion.

The expandable edge 15 of the apparatus 10 may comprise an elastic material such as, but not limited to unsaturated rubber, saturated rubber, thermoplastic elastomers, resilin, elastin, polysulfide, and elastolefin. Utilizing the elastic material, the expandable edge may expand around a portion of an ear and retract to a point where the apparatus may fit snugly (but not constricting) around the portion of the ear. In embodiments, the expandable edge may comprise a fabric portion and an elastic portion, and may also have an elastic portion covered by a fabric portion. The top and bottom portions 12, 16 may include a different or similar elastic material as the middle portion 17, with the differing elasticity levels the result of greater amounts of such an elastic material present within a smaller area or volume within those top and bottom portions than within the middle portion. In embodiments, such middle portion 17 materials may be the same elastic material with the top and bottom portions 12, 16 including packed elastic within a fabric cover such that the rounded edges thereof contort to increase force around a wearer's outer auricle (for the top portion 12) and lobe (for the bottom portion 16) while the middle portion remains as a cover of a portion of the middle outer ear of the wearer alone (or in contact thereof, but without any dominant strength or force applying to the ear for retention purposes). portion may be a continuous loop and may mimic any contour of the opening of the apparatus. The fabric portion may wrap around the elastic portion and may be affixed to at least one of the bottom elastic portion and the elastic portion. In embodiments, the elastic portion may comprise a substantially circular cross section. In embodiments, the elastic portion may comprise a substantially rectangular cross section. In embodiments, the expandable edge may not be elastic.

In embodiments, the expandable edge 15 may comprise a material with a high coefficient of friction affixed to the bottom portion 16. When the apparatus 10 is placed adjacent an ear 11, the expandable edge 15 may provide a frictional force between the material and the ear 11 so that the apparatus 10 may be held securely to the ear 11. In embodiments, the material may comprise a coefficient of friction greater than 0.6. In embodiments, the material may comprise a coefficient of friction greater than 0.8. In embodiments, the material may be textured. A textured material may provide additional surface area contact with an ear which may translate into additional frictional force on the ear. This may more securely keep the apparatus affixed to the ear. In embodiments, the expandable edge may comprise a material with a high coefficient of friction. In embodiments, the expandable edge may comprise a coating material with a high coefficient of friction.

In embodiments, the expandable edge 15 may comprise at least one contour portion that may produce a form-fitting effect when the apparatus 10 is placed adjacent an ear 11. In embodiments, the expandable edge may comprise a contour-responsive material. The contour-responsive material may contour to the shape of an ear when the apparatus is placed adjacent an ear. In embodiments, the contour-responsive material may be a foam material.

In embodiments, the pouch portion 14 may comprise a crimped fabric. In embodiments, the crimped fabric may cover the expandable edge 15 so that the expandable edge 15 may be crimped in addition to the pouch portion 14. In embodiments, the crimped fabric may be bunched up at the top portion 12 and the bottom portion 16 more than at the middle portion 17, thereby potentially creating the elasticity differentials between such portions.

In embodiments, the apparatus 10 may comprise a two-way stretch fabric that may stretch along a longitudinal axis of the apparatus. In embodiments, the apparatus 10 may comprise a four-way stretch fabric that may stretch along a longitudinal axis and a latitudinal axis of the apparatus.

In embodiments, at least one of the top portion 12, the middle portion 17, and the bottom portion 16 may comprise an elastic fabric. In embodiments, the elastic fabric may comprise at least one of natural fibers and synthetic fibers as well as elastic fibers incorporating elastic polymers such as, but not limited to, unsaturated rubber, saturated rubber, thermoplastic elastomers, resilin, elastin, polysulfide, and elastolefin. Different types of elastic fibers may be utilized within the top portion 12, the middle portion 17, and the bottom elastic portion 16 based on the end use of the apparatus 10. In embodiments, the top portion 12, the middle portion 17, and the bottom portion 16 may separately comprise different types of elastic fibers. In embodiments, at least one of the top portion 12, the middle portion 17, and the bottom portion 16 may comprise an elastic nonwoven fabric.

In embodiments, at least one of the interior portions of the top portion, the middle portion, and the bottom portion may comprise a material with a high coefficient of friction.

FIG. 2 depicts, in more specific detail than above, a side view of an ear cover apparatus 10 in accordance with embodiments. In this embodiment, the pouch portion 14 may be substantially semicircular. In embodiments, the pouch portion 14 may be substantially half-moon shaped. The apparatus may cover a substantial portion of the helix of the ear 11 but may not cover the entirety of the ear canal 13.

Figure 4:
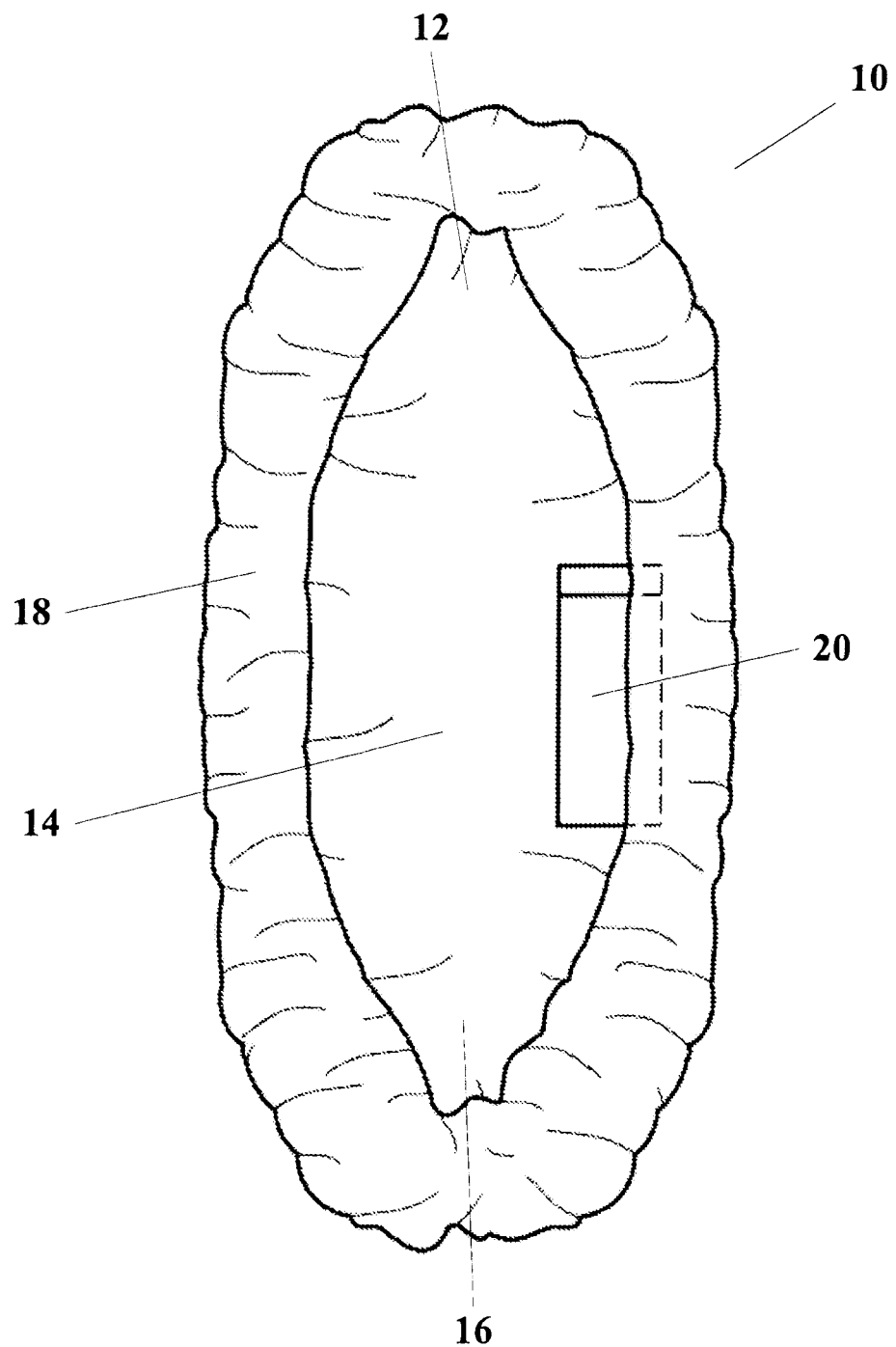
FIG. 4 depicts a front interior view of an ear cover implement with a pocket for introduction of a communication device therein in accordance with embodiments.
Figure 5:
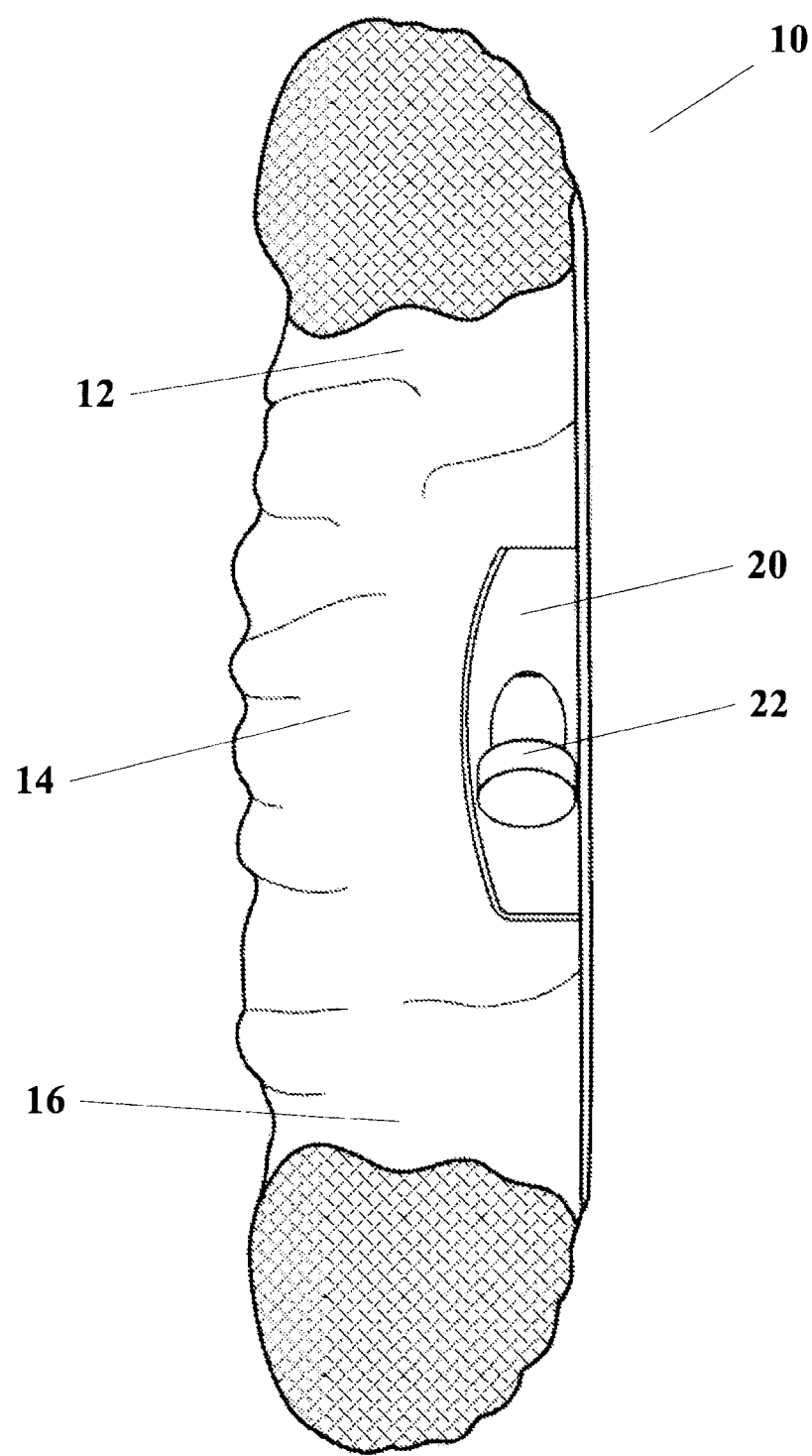
FIG. 5 depicts a rear exterior view of the ear cover of FIG. 4.

FIGS. 4 and 5 depicts different views of an ear cover apparatus 10 including an interior pocket 20 in accordance with embodiments. The interior pocket 20 may be either partially or fully encompassed within the pouch portion of the apparatus and may include an opening 24, an interior surface 26, and an exterior surface 28. In embodiments, at least a portion of the exterior surface 28 may be at least one of an interior portion of the top portion 12, the middle portion 17, and the bottom portion 16 of the ear cover 10. In embodiments, the interior pocket 20 may comprise at least one of a woven fabric and a knit fabric. In embodiments, the interior pocket 20 may comprise a nonwoven material. The interior pocket 20 may expand to provide an internal area that may at least partially house items 22 utilized in conjunction with ears such as, but not limited to Bluetooth devices, headphones, and hearing aids. When not in use, the interior pocket may lie flat against a portion of an ear that is not the ear canal. In embodiments, the interior pocket 20 may be sewed to the apparatus. In embodiments, the interior pocket 20 may be ultrasonically bonded to the apparatus. In embodiments, the interior pocket 20 may be needle punched to the apparatus 10.

In embodiments, the interior surface 26 of the interior pocket 20 may comprise a material with a high coefficient of friction. When an item is placed at least partially within the interior pocket 20, the interior surface 26 may provide a frictional force between the material and the item 22 so that the at least a portion of an item may be held securely within the interior pocket 20. The material may be similar to the material that may be used in embodiments for the expandable edge of the apparatus. In embodiments, the material may be textured. A textured material may provide additional surface area contact with an item which may translate into additional frictional force on the item. This may more securely keep the item within the interior pocket.

In embodiments, the opening 24 of the interior pocket 20 may run along an interior pocket axis aligned parallel with an apparatus opening axis.

The disclosure may further provide an ear cover system. In embodiments, the system may comprise a pouch portion including a top portion, a middle portion, a bottom portion, an opening, and an expandable edge circumnavigating the periphery of the opening. Each of the top portion, the middle portion, and the bottom portion may comprise an interior surface and an exterior surface. The opening may provide a space through which a portion of an ear may be at least partially engulfed by the apparatus. The system may further comprise an interior pocket encompassed within the pouch portion. A portion of an electronic device may be at least partially housed within the interior pocket. The top portion and bottom portion may be greater in elasticity than the middle portion. Elongation of the apparatus may allow for a number of different sized ears to at least partially fit within the apparatus. In embodiments, the apparatus may provide coverage to at least one portion of an ear adjacent an ear canal.

In embodiments, the aforementioned embodiments of a system may comprise any previously mentioned aspects that the embodiments of apparatuses may provide.

In embodiments, the ear cover apparatus may be utilized in conjunction with human ears and are applied thereto through insertion of the target auricle and lobe within the pouch and securing the top portion over such outer auricle thereof and the bottom portion thereof over the lobe thereof. The ear canal is thus left open to at least a certain degree to permit the user to listen for external sounds, if needed. Thus, upon such placement and retention on a target wearer's ear or ears, the implement accords protection from heat (such as, as alluded to above, a bonnet hair dryer), cold wind and air (to supplant an ear muff that covers the entirety of an ear; the currently disclosed implement accords the user coverage of the sensitive areas of the outer ear while, again, leaving the ear canal open for hearing purposes), and even, if desired, ultraviolet radiation (to supplement or replace sunblock lotions and other like formulations applied thereto the outer ear surfaces; to that end, the ear cover itself may be coated, impregnated, or otherwise treated with a proper UV-A and.or UV-B blocking composition to assist in such a situation). The retention capabilities, with the protective qualities, particularly through the insulative properties of the fabric and elastic constituents therein, thus accords a user a versatile overall ear cover that sufficient protects, allows for effective hearing while in place, and stays reliably applied thereto a wearer's outer ear, in relation to the descriptions provided herein.

In embodiments, ear cover apparatuses may be provided in varying sizes in order to accommodate a plurality of ear sizes. As noted above, however, the shapes thereof may be uniform to allow for application to either side ear for a wearer without need for determination of anything further prior to implementation.

In embodiments, an electronic device may comprise devices such as, but are not limited to headphones, Bluetooth devices, and hearing aids. Thus, if utilized the pocket may be configured to hold any such electronic device to permit access to the at least partially uncovered ear canal (by the ear cover itself) to accommodate desired communication/listening capabilities in this manner.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention.

What I claim is:

1. An ear cover apparatus comprising a crimped fabric pouch having a top portion comprising an elastic fabric material and having an interior surface and an exterior surface;
   a middle portion comprising said crimped fabric material an interior surface and an exterior surface, a bottom portion comprising an elastic fabric material and having an interior surface and an exterior surface, an opening adjacent said interior surface of said top portion, said interior surface of said middle portion, and said interior surface of said bottom portion, said opening including a periphery; and an expandable edge circumnavigating said periphery of said opening, said expandable edge comprising rubber; wherein said middle portion has less an elasticity than an elasticity of said top and bottom portions; wherein said ear cover apparatus is configured to provide coverage to at least one portion of a wearer's ear adjacent said wearer's ear canal when worn by said wearer with said top portion at least partially around said wearer's pinna in relation to said elastic fabric material and said bottom portion at least partially around said wearer's lobe in relation to said elastic fabric material; and wherein said ear cover apparatus is configured to leave said wearer's ear canal at least partially exposed when worn by said wearer.

2. The apparatus of claim 1, wherein said expandable edge comprises at least a portion of a material comprising a coefficient of friction greater than 0.6.

3. The apparatus of claim 2, wherein said at least a portion of a material comprising exhibits a coefficient of friction greater than 0.8.

4. The apparatus of claim 1, further comprising an interior pocket encompassed within said crimped fabric pouch.

5. A method for affixing an ear cover to an ear and an electronic device comprising:
   i) providing said an ear cover apparatus of claim 1; and
   ii) affixing said ear cover apparatus to said auricle wearer's ear wherein said top portion at least partially surrounds said wearer's pinna, wherein said bottom portion at least partially surrounds said wearer's lobe, and wherein said ear cover apparatus leaves said wearer's ear canal at least partially exposed.

6. The method of claim 5, wherein said expandable edge comprises at least a portion of a material comprising a coefficient of friction greater than 0.6.

7. The method of claim 6, wherein said at least a portion of a material comprising exhibits a coefficient of friction greater than 0.8.

8. A method for affixing an ear cover apparatus including an electronic device therein to a wearer's ear, said method comprising the steps of:
   i) providing said an ear cover apparatus of claim 4;
   ii) inserting at least a portion of the electronic device into said interior pocket; and
   iii) affixing said ear cover apparatus to said wearer's ear wherein said top portion at least partially surrounds said wearer's pinna, wherein said bottom portion at least partially surrounds said wearer's lobe, and wherein said ear cover apparatus leaves said wearer's ear canal at least partially exposed.

9. The method of claim 8, wherein said expandable edge comprises at least a portion of a material comprising a coefficient of friction greater than 0.6.

10. The method of claim 9, wherein said at least a portion of a material comprising exhibits a coefficient of friction greater than 0.8.

\* \* \* \* \*